United States Patent [19]

Sugimoto

[11] Patent Number: 4,537,852

[45] Date of Patent: Aug. 27, 1985

[54] PROCESS FOR THE PRODUCTION OF HUMAN UROKINASE

[75] Inventor: Kaname Sugimoto, Okayama, Japan

[73] Assignee: Kabushiki Kaisha Hayashibara Seibutsu Kagaku Kenkyujo, Okayama, Japan

[21] Appl. No.: 320,746

[22] Filed: Nov. 12, 1981

[30] Foreign Application Priority Data

Dec. 5, 1980 [JP] Japan .............................. 55-171588

[51] Int. Cl.$^3$ .................... C12N 9/72; C12N 15/00; C12N 5/00; C12R 1/91
[52] U.S. Cl. .............................. 435/215; 435/172.2; 435/240; 435/241; 435/948; 424/94; 935/99; 935/109; 935/34
[58] Field of Search .................... 435/2, 68, 215, 172, 435/240, 241, 269, 948; 424/93, 94

[56] References Cited

U.S. PATENT DOCUMENTS

| | | | |
|---|---|---|---|
| 4,195,125 | 3/1980 | Wacker | 435/172 |
| 4,232,124 | 11/1980 | Mann | 435/215 |
| 4,242,460 | 12/1980 | Chick et al. | 435/284 |
| 4,276,282 | 6/1981 | Sugimoto | 424/85 |
| 4,285,929 | 8/1981 | Sugimoto | 424/85 |
| 4,328,207 | 5/1982 | Sugimoto | 424/85 |
| 4,328,314 | 5/1982 | Horiguchi et al. | 435/240 |
| 4,352,883 | 10/1982 | Lim | 435/240 |
| 4,377,513 | 3/1983 | Sugimoto | 26/112 R |
| 4,383,034 | 5/1983 | Sugimoto | 435/68 |
| 4,383,035 | 5/1983 | Sugimoto | 435/68 |
| 4,383,036 | 5/1983 | Sugimoto | 435/68 |

FOREIGN PATENT DOCUMENTS 0005644  11/1979  European Pat. Off. ............ 435/241

OTHER PUBLICATIONS

Zeleznik et al., "Production of Long Term Steroid--Producing Granulosa Cell Cultures by Cell Hybridization", Endocrinology 105(1), (1979), pp. 156-162.
Bordelon et al., "Human Glycoprotein Horomone Production in Human-Human Somatic Cell Hybrids", Experimental Cell Research 103(2), (1976), pp. 303-310, Chem. Abst. 86: 53094r.
Markus et al., "Content and Characterization of Plasminogen Activators in Human Lung Tumors and Normal Lung Tissue", Cancer Research 40(3), (1980), pp. 841-848, Chem. Abst. 92: 144676x.
Wilsonet et al., "Molecular Species of Plasminogen Activators Secreted by Normal and Neoplastic Human Cells", Cancer Research 40(3), (1980), pp. 933-938, Chemical Abstracts 92: 144679a.
Bernik et al., "Production by Human Tissues in Culture of Immunologically Distinct, Multiple Molecular Weight Forms of Plasminogen . . . ", Ann. N.Y. Academy of Sciences, 370, (1981), pp. 592-608, Chem Abst. 95: 94388u.
Shin, "Use of Nude Mice for Tumorigenicity Testing and Mass Propagation", Methods in Enzymology, vol. LVIII, pp. 370-379.
Kennett, "Cell Fusion", Methods in Enzymology, vol. LVIII, (1979), pp. 345-351.
Allan et al., "Co-Expression of Differentiation Markers in Hybrids Between Friend Cells and Lymphoid Cells and the Influence of . . . ", Cell, vol. 19, (1980), pp. 437-447.
Deisseroth et al., "Hemoglobin Synthesis in Somatic Cell Hybrids: & Globin Gene Expression in Hybrids Between Mouse . . . ", Proceedings of the National Academy of Sciences, 72(3), 1975), pp. 1102-1106.
Lewis, "Plasminogen Acticator (Urokinase) from Cultured Cells", Thromb. Haemostasis 42(3), (1979), pp. 895-900, Chem. Abst. 92: 55678g.
Udris, et al., "Diagnosis of the Gravity of Acute Leukemia", U.S.S.R. Pat. No. 648,206, Chemical Abstracts 90:166249.
Rothblat et al., "Growth, Nutrition, and Metabolism of Cells in Culture", vol. II, Academic Press, NY 1978, pp. 224-243.
Knazek, "Solid Tissue Masses Formed in Vitro from Cells Cultured on Artificial Capillaries", Federation Proceedings 33(8), pp. 1978-1981, (1974).
Goding, "Antibody Production by Hybridomas", Journal of Immunological Methods, 39, pp. 285-308, (1980).
Ponten, J., et al., "Morphological and Virological Investigation of Human Tissue Cultures Transformed with SV$_{40}$", J. of Cellular and Comparative Physiology, vol. 61, 145-154, (1963).
Pattillo, "Hormone Synthesis and Function in vitro", Growth, Nutrition and Metabolism of Cells in Culture, 1972, Academic Press, N.Y., 225-227.
Lewin, Gene Expression, Wiley & Sons, pp. 259-265, 1980.

Primary Examiner—Thomas G. Wiseman
Assistant Examiner—John E. Tarcza
Attorney, Agent, or Firm—Browdy and Neimark

[57] ABSTRACT

The present invention relates to a process for the production of human urokinase. More precisely, the present invention relates to a process for the mass production of human urokinase, comprising in vivo multiplication of human cells capable of producing human urokinase, using the nutrient body fluid of a non-human warm-blooded animal, and exposure of the multiplied human cells to an urokinase inducer. The human urokinase present production according to the invention is much higher than that attained by conventional methods; thus, human urokinase can be used in sufficient amount in the prevention and treatment of human diseases.

22 Claims, No Drawings

PROCESS FOR THE PRODUCTION OF HUMAN UROKINASE

The present invention relates to a process for the production of human urokinase.

Urokinase (E.C.3.4.99.26) is an enzyme found in mammalian urine which catalyzes the cleavage of plasminogen into plasmin.

Various types of thrombosis are responsible for an increasing number of deaths each year. This has resulted in an increase in the need for agents containing urokinase. Although conventional processes for the production of human urokinase, such as those by collection from human urine with a flocculant or adsorbent, or by continuous cultivation of human kidney cells in the presence of a urokinase inducer, are known, they do not provide sufficient quantity of low-cost human urokinase to meet demand.

The present inventor has investigated processes for the mass production of low-cost human urokinase. These efforts have resulted in the unexpected finding that human cells obtained by multiplying human cells capable of producing human urokinase, using a non-human warm-blooded animal, have a much higher human urokinase producibility than those obtained by in vitro tissue culture; up to about 2–50-fold of the latter in terms of human urokinase production per cell.

Particularly, the present invention relates to a process for the production of human urokinase, characterized in multiplying human cells capable of producing human urokinase by transplanting said cells to a non-human warm-blooded animal body, or alternatively by allowing said cells to multiply with a device by which the nutrient body fluid of a non-human warm-blooded animal is supplied to said cells, and exposing the human cells multiplied by either of the above multiplication procedures to a urokinase inducer to induce said enzyme.

The process according to the present invention, besides realizing a higher human urokinase production, requires no or much less nutrient medium containing expensive serum for cell multiplication, and renders much easier the maintenance of the culture medium during the cell multiplication than in the case of in vitro tissue culture. Particularly, any human cells capable of producing human urokinase can be multiplied easily while utilizing the nutrient body fluid supplied from the non-human warm-blooded animal body by transplanting said cells to the animal body, or suspending said cells in a conventional diffusion chamber devised to receive the nutrient body fluid, and feeding the animal in the usual way. Also, the process is characterized by stabler and higher cell multiplication, and higher human urokinase production per cell.

As to the human cells usable in the present invention, any human cells can be used so far as they produce human urokinase and multiply easily in the non-human warm-blooded animal body. For example, normal kidney cells or lung fibroblast cells, those transformed with radiation or virus, liver carcinoma cells, bladder carcinoma cells, epidermoid carcinoma cells, lung carcinoma cells, fibroma cells, rhabdomyosarcoma cells, mesenchymal sarcoma cells, and established cell lines of the above cells are advantageously feasible in the present invention.

The use of easily maintainable human lymphoblastoid lines introduced with human urokinase production governing genetic sites by means of cell fusion using polyethylene glycol or Sendai virus, or by genetic recombination techniques using DNA ligase, nuclease and DNA polymerase, results in a much or more higher cell multiplication and in an about 2–10-fold higher human urokinase production per cell. Also, since the use of the human lymphoblastoid lines results in the formation of massive tumors which can be easily disaggregated after the cells are transplanted to the non-human warm-blooded animal body, said massive tumors are hardly contaminated with the host animal cells, the multiplied viable human cells can be harvested easily.

As to the non-human warm-blooded animals usable in the present invention, any non-human warm-blooded animals can be used so far as the human cells multiply therein. For example, poultries such as chicken and pigeon, and mammalians such as dog, cat, monkey, goat, pig, cow, horse, rabbit, guinea pig, rat, hamster, mouse and nude mouse are advantageously usable in the present invention. Since the cell transplantation of the human cells to the animal body elicits undesirable immunoreaction, the use of a newborn or infant animal, or those in the youngest possible stage, for example, egg, embryo or fetus, is desirable. In order to reduce the immunoreaction, prior to the cell transplantation, the animal may be treated with X-ray or γ-ray irradiation, about 200–600 rem, or injection of antiserum or immunosuppressive agent prepared according to conventional methods. Since nude mouse, used as the non-human warm-blooded animal, exhibits weaker immunoreaction even when in its adulthood, conveniently, any established human cell lines can be transplanted therein, and multiplied rapidly without such pretreatment.

Stabilized cell multiplication and enhancement of human urokinase production can be both carried out by repeated transplantation using combination(s) of different non-human warm-blooded animals; for example, the objectives are attainable first by implanting the cells in hamster and multiplying therein, then by reimplanting in nude mouse. The repeated transplantation may be carried out with animals of the same class or division as well as those of the same species or genus.

As to where the human cells are implantable, the human cells can be implanted in any sites of the animal so far as the cells multiply therein; for example, in the allantoic cavity, or intravenously, intraperitoneally, or subcutaneously.

Besides direct transplantation of the human cells to the animal body, any of the conventional human cell lines can be multiplied easily while utilizing the nutrient body fluid supplied from the animal body by embedding, for example, intraperitoneally, in the animal body a conventional diffusion chamber, of any of various shapes and sizes, and equipped with a porous membrane filter, ultra filter or hollow fiber having a pore size of about $10^{-7}$ to $10^{-5}$ m in diameter which prevents contamination with the host animal cells into the chamber. The diffusion chamber can be designed, if necessary, so it could be placed, for example, on the host animal, and the body fluid from the animal body allowed to circulate into the chamber, thus enabling observation of the cell suspension in the chamber through transparent side window(s), equipped on the chamber wall(s), and enabling replacement and exchange with a fresh chamber. Cell production per host thereby increases to a further higher level over the period of the animal life without any sacrifice of the host animal. Furthermore, when such a diffusion chamber is used, since the immunoreaction is not elicited due to the absence of direct contact of the human cells with the host animal cells, any non-human warm-blooded animal can be used without the pretreatment to reduce immunoreaction, and the multiplied human cells can be harvested easily.

Feeding of the animal implanted with the human cells can be carried out by conventional methods even after the cell transplantation, and no special care is required.

Maximum cell multiplication can be attained within 1-20 weeks after the cell transplantation. When the established human cell line implanted in the animal is human lymphoblastoid line or human tumor cell, the maximum cell multiplication can be attained within 1-5 weeks after the cell transplantation.

According to the present invention, the number of the human cells obtained per host ranges from about $10^7$ to $10^{12}$ or more. In other words, the number of the human cells transplanted to the animal increases about $10^2$–$10^7$-fold or more, or about $10^1$–$10^6$-fold or more than that attained by in vitro tissue culture using nutrient medium; thus, the cells are suitable for the human urokinase production.

As to the method for human urokinase induction, any method can be employed so far as the human cells release human urokinase thereby. For example, the human cells, obtained by multiplying in ascite in suspension and harvesting from said ascite, or by extracting the massive tumor formed subcutaneously and harvesting after the disaggregation of the massive tumor, are suspended to give a cell concentration of about $10^4$–$10^8$ cells per ml in a nutrient medium, prewarmed at a temperature of about 20°–40° C., and then subjected to an urokinase inducer at this temperature for several hours or days to induce human urokinase.

Preferable urokinase inducers are amino acids such as glycine and phenylalanine; saccharides such as glucose, inositol, ribose and deoxyribose; and hormones such as Adrenalin (epinephrine). During the human urokinase induction, the stabilization of the released urokinase and enhancement of human urokinase production may be both carried out by the addition of a stabilizer and/or agent such as pronase (E.C.3.4.24.4) or alkaloids.

The human urokinase thus obtained can be collected easily by purification and separation techniques using conventional procedures such as salting-out, dialysis, filtration, centrifugation, concentration and lyophilization. If a further purified human urokinase preparation is desirable, a preparation of the highest purity can be obtained by the above mentioned techniques in combination with other conventional procedures such as adsorption and desorption with ion exchange, gel filtration, affinity chromatography, isoelectric point fractionation and electrophoresis.

The human urokinase obtained according to the present invention is immunologically identical with that from human urine, and not contaminated with pyrogen or hepatitis virus. Therefore, the human urokinase can be used advantageously alone or in combination with one or more agents, for example, steroid hormone, anticoagulant or antitumor agent, for injection administration in the prevention and treatment of human diseases.

Throughout the whole specification, the fibrinolytic activity of the human urokinase was determined by the fibrin plate assay method as described in Ploug et al., Biochem. Biophys. Acta, Vol. 24, page 278 (1957), and expressed by the International Unit (IU).

Several embodiments of the present invention are disclosed hereinafter.

EXAMPLE 1

Adult nude mice were implanted subcutaneously with a human rhabdomyosarcoma line TE-32RD, and then fed in the usual way for four weeks. The resulting massive tumors, formed subcutaneously and about 10 g each, were extracted and disaggregated by mincing and suspending in a physiological saline solution containing trypsin. After washing the cells with Earle's 199 medium (pH 7.2), supplemented with 10 v/v % foetal calf serum, the cells were resuspended to give a cell concentration of about $1 \times 10^5$ cells per ml in a fresh preparation of the same medium which contained 50 mM L-glycine as the urokinase inducer, and then incubated at 37° C. for ten days to induce human urokinase. Thereafter, the cells were ultra-sonicated, and the fibrinolytic activity in the supernatant was determined. The human urokinase production was about 4,000 IU per ml cell suspension.

Control cells, obtained by cultivating in vitro the human rhabdomyosarcoma line at 37° C. with Parker's 199 medium (pH 7.2), supplemented with 10 v/v % foetal calf serum, were treated similarly as above to induce human urokinase. The human urokinase production was only about 750 IU per ml cell suspension.

EXAMPLE 2

The human rhabdomyosarcoma line TE-32RD and a human Namalwa leukemic lymphoblastoid line were suspended together in a vessel with a salt solution, containing 140 mM NaCl, 54 mM KCl, 1 mM $NaH_2PO_4$ and 2 mM $CaCl_2$, to give a respective cell concentration of about $10^3$ cells per ml. The ice-chilled cell suspension was mixed with a fresh preparation of the same salt solution containing UV-irradiation preinactivated Sendai virus, transferred into a 37° C. incubator five minutes after the mixing, and stirred therein for 30 minutes to effect cell fusion, introducing the human urokinase producibility of the human rhabdomyosarcoma line into the human leukemic lymphoblastoid line. After cloning according to conventional methods the hybridoma cell strain capable of producing human urokinase, the hybridoma cell strain was implanted intraperitoneally in adult nude mice which were then fed in the usual way for five weeks. The resulting massive tumors, about 15 g each, were extracted and treated similarly as in EXAMPLE 1 to induce human urokinase except that 50 mM L-glycine was replaced with 0.1 w/v % phenylalanine and 0.1 w/v % glucose. The human urokinase production was about 12,000 IU per ml cell suspension.

A control experiment was carried out similarly as in EXAMPLE 1 by cultivating in vitro the fused human Namalwa leukemic lymphoblastoid line, and exposing the multiplied human cells to the urokinase inducer. The human urokinase production was only about 1,000 IU per ml cell suspension.

EXAMPLE 3

After injection of antiserum, prepared with rabbit according to conventional methods, into newborn hamsters to reduce their immunoreaction, the animals were implanted subcultaneously with a human JBL leukemic lymphoblastoid line wherein the human urokinase producibility of a human lung carcinoma line A-549 was introduced similarly as in EXAMPLE 2, and then fed in the usual way for three weeks. The resulting massive tumors, formed subcutaneously and about 10 g each, were extracted and treated similarly as in EXAMPLE 1 to induce human urokinase. The human urokinase production was about 14,000 IU per ml cell suspension.

A control experiment was carried out similarly as in EXAMPLE 1 by cultivating in vitro the fused human JBL leukemic lymphoblastoid line, and exposing the multiplied human cells to the urokinase inducer. The human urokinase production was only about 900 IU per ml cell suspension.

EXAMPLE 4

Newborn rats were implanted intravenously with a human Namalwa leukemic lymphoblastoid line wherein the human urokinase producibility of the human rhabdomyosarcoma line TE-32RD was introduced similarly as in EXAMPLE 2, and then fed in the usual way for four weeks. The resulting massive tumors, about 40 g each, were extracted and treated similarly as in EXAMPLE 2 to induce human urokinase. The human urokinase production was about 12,000 IU per ml cell suspension.

A control experiment was carried out similarly as in EXAMPLE 1 by cultivating in vitro the fused human Namalwa leukemic lymphoblastoid line, and exposing the multiplied human cells to the urokinase inducer. The human urokinase production was only about 600 IU per ml cell suspension.

EXAMPLE 5

After about 400 rem X-ray irradiation of adult mice to reduce their immunoreaction, the animals were implanted subcutaneously with the human rhabdomyosarcoma line TE-32RD, and then fed in the usual way for four weeks. The resulting massive tumors, formed subcutaneously and about 15 g each, were extracted and treated similarly as in EXAMPLE 1 to induce human urokinase. The human urokinase production was about 5,000 IU per ml cell suspension.

A control experiment was carried out similarly as in EXAMPLE 1 by cultivating in vitro the human rhabdomyosarcoma line, and exposing the multiplied human cells to the urokinase inducer. The human urokinase production was only about 800 IU per ml cell suspension.

EXAMPLE 6

A human JBL leukemic lymphoblastoid line wherein the human urokinase producibility of the human lung carcinoma line A-549 was introduced similarly as in EXAMPLE 3 was suspended in physiological saline solution, transferred into a plastic cylindrical diffusion chamber, inner volume about 10 ml, and equipped with a membrane filter having a pore size of about $0.5\mu$. After intraperitoneal embedding of the chamber into an adult rat, the animal was fed in the usual way for four weeks, and the chamber was removed. The human cell density in the chamber attained by the above operation was about $2 \times 10^9$ cells per ml which was about $10^3$-fold or more higher than that attained by in vitro cultivation using a $CO_2$ incubator. The human cells thus obtained were treated similarly as in EXAMPLE 2 to induce human urokinase. The human urokinase production was about 21,000 IU per ml cell suspension.

A control experiment was carried out similarly as in EXAMPLE 1 by cultivating in vitro the fused human JBL leukemic lymphoblastoid line, and exposing the multiplied human cells to the urokinase inducer. The human urokinase production was only about 900 IU per ml cell suspension.

EXAMPLE 7

A human JBL leukemic lymphoblastoid line wherein the human urokinase producibility of the human lung carcinoma line A-549 was introduced similarly as in EXAMPLE 3 was implanted in allantoic cavities of embryonated eggs which had been preincubated at 37° C. for five days. After incubation of the eggs at this temperature for an additional one week, the multiplied human cells were harvested. The human cells were treated similarly as in EXAMPLE 2 to induce human urokinase. The human urokinase production was about 8,500 IU per ml cell suspension.

A control experiment was carried out similarly as in EXAMPLE 1 by cultivating in vitro the fused human JBL leukemic lymphoblastoid line, and exposing the multiplied human cells to the urokinase inducer. The human urokinase production was only about 900 IU per ml cell suspension.

What we claim is:

1. A process for producing human urokinase, comprising:
    fusing parent human cells inherently capable of producing human urokinase with a human lymphoblastoid line to obtain hybridoma cells capable of producing human urokinase;
    implanting said hybridoma cells in an immunodeficient or immunosuppressed non-human warm-blooded animal;
    feeding the animal to allow said hybridoma cells to utilize the nutrient body fluid of the animal for their multiplication;
    extracting and disaggregating the resultant tumor, formed in the animal, to obtain the multiplied hybridoma cells;
    culturing the multiplied hybridoma cells on an in vitro nutrient medium in the presence of an effective amount of a urokinase inducer under conditions appropriate to accumulate a substantial amount of human urokinase; and
    recovering the accumulated human urokinase from the culture.

2. A process according to claim 1, wherein said fusing step comprises the steps of:
    suspending said parent human cells inherently capable of producing human urokinase together with said human lymphoblastoid line in a salt solution containing an effective amount of a cell fusion inducing agent;
    allowing the resultant cell suspension to stand for a period sufficient to effect cell fusion; and
    selecting or cloning one or more hybridoma lines having a human urokinase producibility higher than that of the parent human cells.

3. A process in accordance with claim 2, wherein said cell fusion inducing agent is inactivated Sendai virus or polyethylene glycol.

4. A process as set forth in claim 1, wherein said parent cells are normal kidney or lung cells.

5. A process as set forth in claim 1, wherein said parent cells are selected from the group consisting of liver carcinoma cells, bladder carcinoma cells, epidermoid carcinoma cells, lung carcinoma cells, fibrinoma cells, rhabdomyosarcoma cells, and mesenchymal sarcoma cells.

6. A process according to claim 2, wherein said human lymphoblastoid line is of human leukemic origin.

7. A process according to claim 2, wherein said human lymphoblastoid line is a member selected from the group consisting of Namalwa, BALL-1 and JBL.

8. A process as set forth in claim 1, wherein said non-human warm-blooded animal is a mammalian or fowl.

9. A process as set forth in claim 1, wherein said urokinase inducer is a member selected from the group consisting of amino acids, saccharides, hormones and mixtures thereof.

10. A process as set forth in claim 1, wherein said urokinase inducer is selected from the group consisting of glycine, phenylalanine, glucose, inositol, ribose, deoxyribose, epinephrine, and mixtures thereof.

11. A process as set forth in claim 1, wherein said non-human warm-blooded animal is a chicken, pigeon, dog, cat, monkey, goat, pig, cow, horse, rabbit, guinea pig, rat, hamster, nude mouse or mouse.

12. A process for producing human urokinase, comprising:
   fusing parent human cells inherently capable of producing human urokinase with a human lymphoblastoid line to obtain hybridoma cells capable of producing human urokinase;
   suspending said hybridoma cells in a diffusion chamber capable of permitting the nutrient body fluid of a non-human warm-blooded animal to to supplied to said hybridoma cells;
   embedding or placing said chamber in or on a non-human warm-blooded animal in a manner such that the nutrient body fluid of said animal is supplied to the cells within said chamber;
   feeding said animal to allow said hybridoma cells to utilize the nutrient body fluid for their multiplication;
   collecting the multiplied hybridoma cells from said chamber;
   culturing the multiplied hybridoma cells on an in vitro nutrient medium in the presence of an effective amount of a urokinase inducer under conditions appropriate to accumulate a substantial amount of human urokinase; and
   recovering the accumulated human urokinase from the culture.

13. A process according to claim 12, wherein said fusing step comprises the steps of:
   suspending said parent human cells inherently capable of producing human urokinase together with said lymphoblastoid line in a salt solution containing an effective amount of a cell fusion inducing agent;
   allowing the resultant cell suspension to stand for a period sufficient to effect cell fusion; and
   selecting or cloning one or more hybridoma lines having a human urokinase producibility higher than that of the parent human cells.

14. A process in accordance with claim 13, wherein said cell fusion inducing agent is inactivated Sendai virus or polyethylene glycol.

15. A process as set forth in claim 12, wherein said parent cells are normal kidney or lung cells.

16. A process as set forth in claim 12, wherein said parent cells are selected from the group consisting of liver carcinoma cells, bladder carcinoma cells, epidermoid carcinoma cells, lung carcinoma cells, fibrinoma cells, rhabdomyosarcoma cells, and mesenchymal sarcoma cells.

17. A process according to claim 12, wherein said human lymphoblastoid line is of human leukemic origin.

18. A process according to claim 12, wherein said human lymphoblastoid line is a member selected from the group consisting of Namalwa, BALL-1 and JBL.

19. A process as set forth in claim 12, wherein said non-human warm-blooded animal is a mammalian or fowl.

20. A process as set forth in claim 12, wherein said urokinase inducer is a member selected from the group consisting of amino acids, saccharides, hormones and mixtures thereof.

21. A process as set forth in claim 12, wherein said urokinase inducer is a member selected from the group consisting of glycine, phenylalanine, gluconse, inositol, ribose, deoxyribose, epinephrine, and mixtures thereof.

22. A process as set forth in claim 12, wherein said non-human warm-blooded animal is a chicken, pigeon, dog, cat, monkey, goat, pig, cow, horse, rabbit, guinea pig, rat, hamster, nude mouse or mouse.

* * * * *